United States Patent [19]

Schmitt et al.

[11] Patent Number: 4,950,477

[45] Date of Patent: Aug. 21, 1990

[54] METHOD OF PREVENTING AND TREATING PULMONARY INFECTION BY FUNGI USING AEROSOLIZED POLYENES

[75] Inventors: Heinz J. Schmitt, Millington, N.J.; Donald Armstrong, New York, N.Y.; Edward M. Bernard, Alandale, N.J.

[73] Assignee: Memorial Hospital For Cancer and Allied Dieseas, New York, N.Y.

[21] Appl. No.: 236,040

[22] Filed: Aug. 23, 1988

[51] Int. Cl.$^5$ .............................................. A61K 9/12
[52] U.S. Cl. ..................................... 424/43; 424/117; 424/119; 424/122
[58] Field of Search .................. 424/43, 119, 122, 117

[56] References Cited

PUBLICATIONS

Rodenhuis, S., et al. Invasive Pulmonary Aspergillosis in a Non–Immunosuppressed Patient: Successful Management with Systemic Amphotericin and Flucytosine and Inhaled Amphotericin. Thorax 1984; 39: 78–79.

Hargis, P. L., et al. Intracavitary Amphotericin B in the Treatment of Symptomatic Pulmonary Aspergillomas. Am. J. Med. 1980; 68: 389–394.

Swerdlow, B., Deresinsky, S. Development of Aspergillus Sinusitis in a Patient Receiving Amphotericin B. Am. J. Med. 1984; 76: 162–166.

Walzer, Y., Bear, R. a. Ureteral Obstruction of Renal Transplant Due to Ureteral Condidiasis. Urology 1983; 3: 295–297.

Ezdinli, E. Z., et al. Oral Amphotericin B for Candidiasis in Patients with Hematologic Neoplasms. JAMA 1979; 242: 258–260.

Christiansen, K. J., et al. Distribution and Activity of Amphotericin B in Humans. J. Infect. Dis. 1985; 152: 1037–1043.

McKendrick, D. W., Medlock, J. M. Pulmonary Moniliasis Treated with Nystatin Aerosol. Lancet 1958; 1: 621–622.

Gero, S., Szekely, J. Pulmonary Moniliasis Treated with Nystatin Aerosol. Lancet 1958; 2: 1229–1230.

Kohn, R., Hepler, R. Management of Limited Rhinoorbital Mucormycosis Without Exenteration. Opthalmology 1985; 92: 1440–1444.

Stenson, S., et al. Bilateral Endogenous Necrotizing Scleritis Due to Aspergillus Oryzae. Ann. Ophthalmology 1982; 14: 67–72.

Krakowa, P., et al. Local Treatment of Aspergilloma of the Lung With a Paste Containing Nystatin or Amphotericin B. Tubercle 1970; 51: 184–191.

Schubert, M. M., et al. Head and Neck Aspergilloisis in Patients Undergoing Bone Marrow Transplantation. Cancer 1986; 57: 1092–1096.

Meunier, F., et al. Prophylaxis of Aspergillosis in Neutropenic Cancer Patients with Nasal Spray of Amphotericin B: A Prospective Randomized Study. Program and abstracts of the 27th Interscience Conference on Antimicrobial Agents and Chemotherapy, New York, Oct. 4–7, 1987; Abstract No. 1346.

Domart, Y.; et al. Obstruction des voies urinaires par des bezoars candidosiques ou "fungus balls". Press Medicale 1986; 15: 153–156.

Polsky, B., et al. Intraventricular Therapy of Cryptococcal Meningitis via a Subcutaneous Resevior. Am. J. Med. 1986; 81: 24–28.

Kilburn, K. H. The Innocuousness and Possible Therapeutic Use of Aerosol Amphotericin B. Am. Rev. Resp. Dis. 1959; 80: 441–442.

(List continued on next page.)

Primary Examiner—Ellis P. Robinson
Assistant Examiner—P. L. Prater
Attorney, Agent, or Firm—John P. White

[57] ABSTRACT

This invention concerns a method of preventing a pulmonary infection by a fungus in a subject susceptible to infection by the fungus comprising administering to the subject an amount per dose in an aerosol spray of a polyene or a pharmaceutically acceptable derivative thereof, effective to prevent pulmonary infection by the fungus. This invention further discloses a method of treating pulmonary aspergillosis in a subject comprising administering to the subject an amount per dose in an aerosol spray of a polyene, e.g., amphotericin B or pimaricin, or a pharmaceutically acceptable derivative thereof effective to treat aspergillosis.

43 Claims, 2 Drawing Sheets

OTHER PUBLICATIONS

Viera, D. F., et al. Invasive Pulmonary Aspergillosis After Near-Drowning. Intensive Care Med. 1984; 10: 203-204.

Ikemoto, H., et al. Pulmonary Aspergilloma; Sabouraudia 1971; 9: 30-35.

Schmitt, H. J., et al. MIC and Fungicidal Activity of Terbinafine Against Clinical Isolates of Aspergillus Spp. Antimicrobial Agents Chemotherapy 1988; in press.

Minsker O. B., et al. Treatment of Patients With Pulmonary Aspergillosis by Means of Inhalation of Amphotericin B Aerosols. Probl. Tuberk 1983; 4: 68-69.

Skobel, P., Fungal super Infections of Respitory Organs and Their Treatment by Inhalation and Instillation of Amphotericin B Anti-Infect and Instillation of Amphoterian B Anti-Infect and Moronal Pure Anti Infect Nystatin Anti Infect Human. Med. Welt 1966: 50: 2755-2759.

Boldrey, E. E. Bilateral Endogenous Aspergillus endophthalmitis. Retina 1981; 1: 171-174.

Staib, F., et al. Amphotericin B and Flucytosine Therapy of Aspergillus Pneumonia and Acute Renal Failure. Klin Wochenschr 1987; 65: 40-47.

Law, E. J., et al. Candida Parapsilosis Fungermia in Burn Patients: report of three cases. Burns Incl Therm Inj 1984; 10: 203-206.

Funada, H., et al. Total Intestinal Decontamination for Prevention of Infection in Bone Marrow Transplantation. Japanese Journal of Clinical Oncology 1983; 13 (Suppl 1): 111-126.

Rohatgi, P. K. Pulmonary Sporotrichosis. S Medical Journal 1980; 73: 1611-1617.

Shaikh, B. S. Colonization of Nasal Ulcers as a Source of Candida Parapsilosis. Arch Otolaryngol 1980; 106: 434-446.

Ward, P. H. c et al. Cocidioidomycosis of the Larynx in Infants and Adults, Ann Otol Rhino Laryngol 1977; 86: 655-660.

METHOD OF PREVENTING AND TREATING PULMONARY INFECTION BY FUNGI USING AEROSOLIZED POLYENES

BACKGROUND OF THE INVENTION

Aspergillus spp., notably *Aspergillus fumigatus*, may cause life-threatening infections among transplant recipients and patients receiving therapy for various types of cancer. The most commonly encountered form of disease in these patients is pulmonary aspergillosis (1). Acute fatal sinusitis (2, 3), head and neck involvement (4), cutaneous disease (5) and catheter related infections (6) have also been described.

Invasive pulmonary aspergillosis is difficult to diagnose, even with invasive techniques. Therefore the standard treatment, intravenous amphotericin B, often has to be given empirically—despite its severe toxicity and despite the fact that patients do not tolerate it well. Moreover, amphotericin B is not always effective, and correction of the underlying disorder (e.g. resolution of granulocytopenia) is usually required to achieve a favorable outcome.

In one study involving seven subjects with pulmonary aspergillosis, Ikemoto, et al reported that the treatment of choice in patients with repeated episodes of haemoptysis is surgical excision (33). The authors also reported that treatment with amphotericin B by aerosol inhalation in two patients was unsuccessful, probably because the drug could not reach the apex of the lung in this form.

It has also been reported that treatment of invasive pulmonary aspergillosis was successful using a combination of amphotericin B and 5-flurocytosine administered intravenously and by inhalation (32, 34).

In a study of distribution and activity of amphotericin B in humans, found the highest concentrations of drug was found in the liver, spleen and kidneys (7). Concentrations above 7 mcg per gram of lung tissue were only seen in patients who had received at least 1.7 g of amphotericin B. This data also suggested, that once amphotericin B accumulated in any organ, it was eliminated slowly.

It is assumed, that a reduction of the number of aspergillus spores inhaled, can reduce the risk of developing invasive aspergillus pneumonia among susceptible hosts (8, 9, 10, 11). Amphotericin B is highly fungicidal against aspergillus spores (12), and has a long half life once it reaches the lung parenchyma.

In a newly developed rat model for pulmonary aspergillosis (13) aerosol amphotericin B (aero-AmB) given as prophylaxis (given once, 48 hours prior to infection) or as therapy (given 24 hours after infection, then daily for six days) was evaluated to determine whether had an influence on survival. Other studies were done to determine the pulmonary deposition and fungicidal activity of the drug after aerosol administration.

SUMMARY OF THE INVENTION

This invention concerns a method of preventing a pulmonary infection by a fungus in a subject susceptible to infection by the fungus comprising administering to the subject an amount per dose in an aerosol spray of a polyene or a pharmaceutically acceptable derivative thereof, effective to prevent pulmonary infection by the fungus.

This invention also concerns a method of treating pulmonary aspergillosis in a subject comprising administering to the subject an amount per dose in an aerosol spray of a polyene or a pharmaceutically acceptable derivative thereof effective to treat aspergillosis.

DETAILED DESCRIPTION OF THE INVENTION

Figure 1:
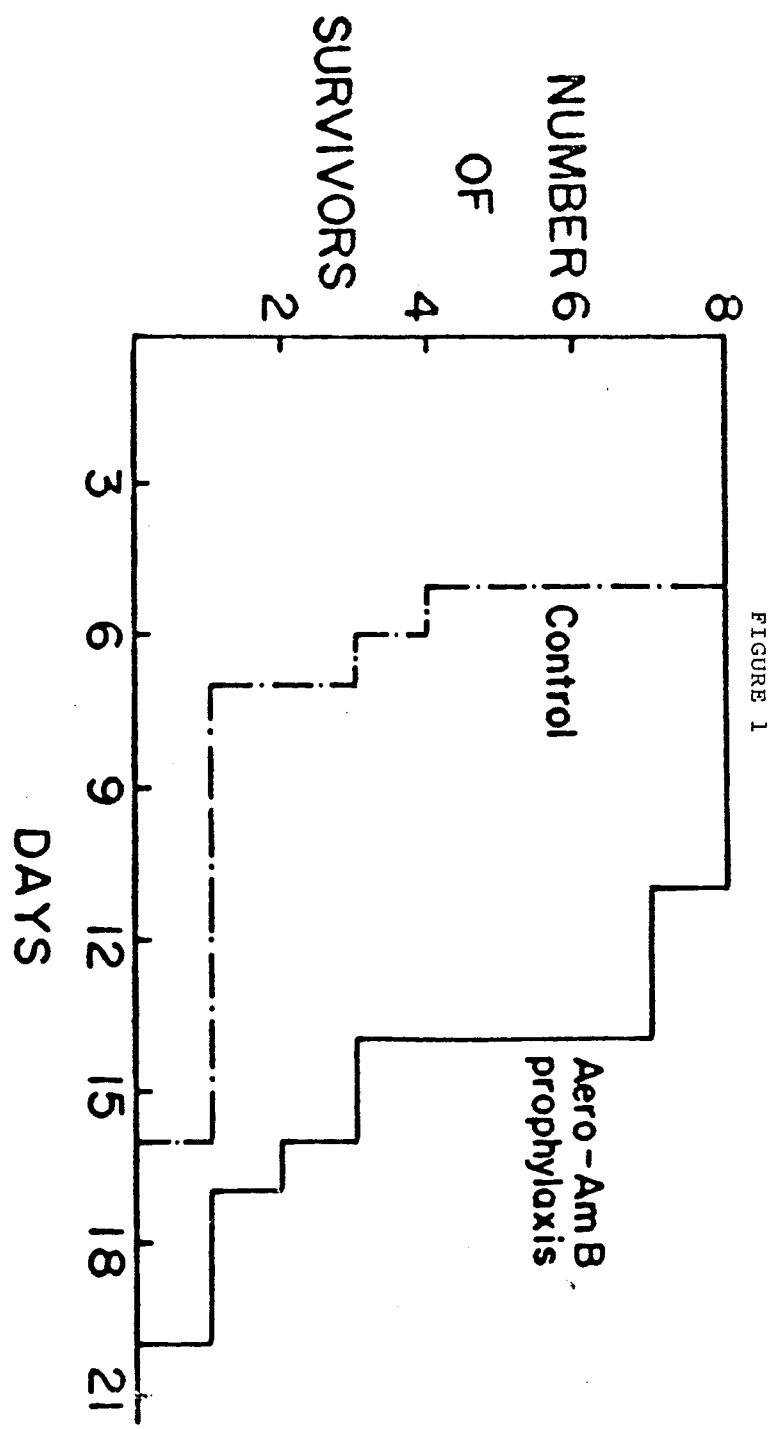
FIG. 1 shows the survival of animals in trial 1. Control animals received no therapy, animals in the aero-AmB group received 1.6 mg/kg aerosolized amphotericin B two days prior to infection.

This invention concerns a method of preventing a pulmonary infection by a fungus in a subject susceptible to infection by the fungus comprising administering to the subject an amount per dose in an aerosol spray of a polyene, e.g., amphotericin B or pimaricin, or a pharmaceutically acceptable derivative thereof effective to prevent pulmonary infection by the fungus. The subject may be any animal but the method is especially suited for a human being. The human being may be susceptible to a pulmonary infection for a number of reasons but is likely susceptible due to immunosuppression. The immunosuppression may be, for example, the result of irradiation or by administration of antimetabolites, antilymphocyte serum, or specific antibody.

The pulmonary infection may be any of a number of infections caused by a fungus including pulmonary aspergillosis. Likewise, the fungus infecting the subject may be any fungus known to those skilled in the art which is capable of causing pulmonary infection. One common such fungus is an Aspergillus especially *Aspergillus fumigatus*.

Pharmaceutically acceptable derivatives of polyenes include any chemical substance derived from polyenes, either directly or by modification or partial substitution. The derivatives may include antifungal polyenes including but not limited to amphotericin B, nystatin and pimaricin.

The polyene or a pharmaceutically acceptable derivative thereof may be administered by intranasal or oral inhalation. The polyene or a pharmaceutically acceptable derivative thereof, may be administered for prevention or treatment of pulmonary infection by a fungus as particles having an aerodynamic diameter between about 0.5 μm and about 8.0 μm. The polyene or a pharmaceutically acceptable derivative thereof may also be administered as particles additionally having a mass median aerodynamic diameter between about 1 μm and about 6 μm. Particles smaller than 0.5 μm are exhaled and thus not retained in the lungs while particles greater than 8.0 μm, such as those produced in an atomizer, do not reach the periphery of the lungs and therefore are not effective in preventing or treating fungal infection in the lungs. The particles are produced by an ultrasonic nebulizer or any devise capable of producing adequate particle sizes.

By administering a polyene or a pharmaceutically acceptable derivative thereof intranasally or by oral inhalation, the toxicity of the polyene or pharmaceutically acceptable derivative thereof that is known to arise from other routes of administration, e.g., intravenous, can be eliminated or minimized.

The amount per dose of the polyene or a pharmaceutically acceptable derivative thereof administered to the subject may be any amount which is effective to prevent pulmonary infection by a fungus including between about 0.01 mg/kg and 6.0 mg/kg. Additionally, the amount per dose of the polyene or a pharmaceutically acceptable derivative thereof administered to the subject may be between about 0.4 mg/kg and about 5.0 mg/kg or between about 0.8 mg/kg and about 4.0 mg/kg. In a preferred embodiment, the amount per dose of the polyene or a pharmaceutically acceptable derivative thereof administered to the subject is between about 1.6 mg/kg and 3.2 mg/kg.

Polyenes may be administered to the subject in any regimen which is effective to prevent pulmonary infection by a fungus including 3 to 14 times in 1 to 6 weeks and thereafter weekly or twice a week. In a further embodiment the polyene is administered daily for 1 week and thereafter is administered twice a week.

The subject invention also concerns a method of treating pulmonary aspergillosis in a subject comprising administering to the subject an amount per dose in an aerosol spray of a polyene or a pharmaceutically acceptable derivative thereof, effective to treat aspergillosis. The subject may be any animal but the method is especially suited for a human being. The aspergillosis may be caused by any of the Aspergillus fungus but is commonly caused by *Aspergillus fumigatus*.

As in preventing fungal infection, treatment may be effected by administering the polyene or a pharmaceutically acceptable derivative thereof by intranasal inhalation or oral inhalation.

In treating a subject, the amount per dose of a polyene or a pharmaceutically acceptable derivative thereof administered to the subject may be any amount which is effective to treat the infection. Amounts of the polyene for treatment of infection are generally somewhat higher than for prevention and include a range of polyene or derivative between about 0.01 mg/kg and 8.0 mg/kg. Additionally, the amount per dose of polyene or a pharmaceutically acceptable derivative thereof administered to the subject may be between about 0.2 mg/kg and about 6.0 mg/kg or between about 0.8 mg/kg and about 5.0 mg/kg especially between about 1.6 mg/kg and about 4.0 mg/kg.

The polyene or a pharmaceutically acceptable derivative thereof is administered in any regimen which is effective to treat the pulmonary fungal infection. In one embodiment the polyene or a pharmaceutically acceptable derivative thereof is administered 1 to 8 times daily, but especially 2 times daily. Additionally, the polyene or a pharmaceutically acceptable derivative thereof may be administered for 7 to 28 days.

This invention also discloses a composition for the prevention or treatment of infection by a fungus, comprising an amount of polyene or a pharmaceutically acceptable derivative thereof in an aerosol spray which comprises particles having an aerodynamic diameter between about 0.5 μm and about 8.0 μm, the composition being effective to prevent or treat pulmonary infection by a fungus, and a pharmaceutically acceptable carrier. The composition may be comprised of at least 55% of the particles having an aerodynamic diameter between about 0.5 μm and about 8.0 μm. The particles additionally may have a mass median aerodynamic diameter between about 1 μm and about 6 μm.

This invention further discloses a composition useful for aerosol administration for the prevention or treatment of infection by a fungus comprising between about 1 mg and about 300 mg of a polyene or a pharmaceutically acceptable derivative thereof. Additionally, the amount of a polyene or the pharmaceutically acceptable derivative thereof may comprise between about 10 mg and about 200 mg or between about 30 mg and about 120 mg.

Finally, this invention discloses a composition useful for aerosol administration for the prevention or treatment of infection by a fungus comprising between about 1 mg and about 100 mg of a polyene or a pharmaceutically acceptable derivative thereof, per ml of a pharmaceutically acceptable carrier. The amount of the polyene or a pharmaceutically acceptable derivative thereof may be between about 10 mg and about 60 mg.

The invention is illustrated in the Experimental Detail and Experimental Discussion sections which follow. These sections are set forth to aid in an understanding of the invention but are not intended to, and shall not be construed to, limit in any way the invention as set forth in the claims which follow thereafter.

Experimental Details

Materials and Methods

Animal Model of Pulmonary Aspergillosis

Male Sprague-Dawley rats (Charles River Breeding Laboratories, Wilmington, Mass.), weighing 125–150 g were treated with cortisone acetate (100 mg/kg s.c.) three times per week throughout the experiment. They also received a low protein diet (8% protein; ICN Biochemicals, Cleveland, OH) and tetracycline (250 mg dissolved in 750 ml drinking water). Animals were infected at the end of week two of this regimen.

*Aspergillus fumigatus* strain H11-20 was isolated from a rat dying of pulmonary aspergillosis while on steroids for production of *pneumocystis carinii* pneumonia. Minimal inhibitory and minimal fungicidal activity as determined by our standard method (12) was 0.8 mcg/ml. The organism was subcultured on Sabouraud-dextrose-agar (SDA). Spores from 5–7 days old cultures were harvested with a 0.02% tween 80 solution and washed in sterile saline. A spore suspension containing $10^7$ spores/ml was produced after counting with a hemocytometer.

Under general anesthesia with ethrane, the trachea of animals was exposed and 0.1 ml of the spore suspension ($10^6$ spores) was injected with a tuberculin syringe. The wound was closed with sutures.

Administration of Aero-AmB

Rats were treated in groups of four or five. They were placed in a glass chamber and this was swept with a stream of aerosolized amphotericin B. The aerosol was generated by air flowing at 8 l/min through the nebulizer (Cadema Medical Products, Middletown, NY). Under these conditions the drug solution was aerosolized at 0.3 ml/min and particles were generated with a mean diameter of 1.0 micron. The dose of aerosol amphotericin B to be given was calculated from the product of the concentration of the drug in the chamber, the minute volume of the rats (lung vol. x resp. rate), and the time of exposure. In all experiments the exposure time was 15 minutes per 4.5 ml of amphotericin B solution administered, and the minute volume of the rats was assumed to be 70 ml.

To deliver a dose of 1.6 mg/kg the nebulizer had to be charged with 4.5 ml of a 5 mg/ml solution of amphotericin B in water. During an exposure time of 15 minutes, 120 l of air and 22.5 mg of amphotericin B flowed through the chamber; the concentration of amphotericin B in the atmosphere of the chamber was thus about 0.19 mcg/ml. This value multiplied by the minute volume and the exposure time gives a dose of 199.5 mcg. Since the rats weighed 0.125 kg, the dose was 1.6 mg/kg per treatment. Doses in all trials were calculated as above. This provides an estimate of the amount of amphotericin B that the animals inhaled; it does not predict the amount of the drug that will be retained in the lungs. Under these conditions 6–10% of the drug should be retained.

Medication

Amphotericin B (Fungizone) was purchased from Squibb & Sons, Princeton, NJ. Stock solutions with a concentration of 5 or 10 mg/ml were made in distilled water and stored in the refrigerator until further use for up to 48 hours.

Results

Characterization of the Animal Model

The animal model produces a progressive bronchopulmonary aspergillosis (13). Mortality among infected animals began after 48 hours and more than 50% of the animals died by day 5. By day 7, 60%–90% of all untreated animals died. Lung weight rose from about 1 g to 2 g within 2–5 days. Numerous hyphae were detectable in smears of lung homogenates. Pathological sections of sacrificed animals on day two or later showed a hyphal bronchopneumonia. Parenteral treatment with amphotericin B was effective in preventing deaths in a dose-dependent fashion; the 100% effective dose (no deaths by day 7) was 4 mg/kg given i.p. once daily.

Effectiveness of Aerosol Amphotericin B

Trial 1. Animals in groups of eight received either no medication (control group) or a single dose of 1.6 mg/kg of aero-AmB, two days prior to infection. Survival was monitored daily. The first death in the aero-AmB group occurred on day 11, by which time ⅞ control animals had died (FIG. 1).

Figure 2:
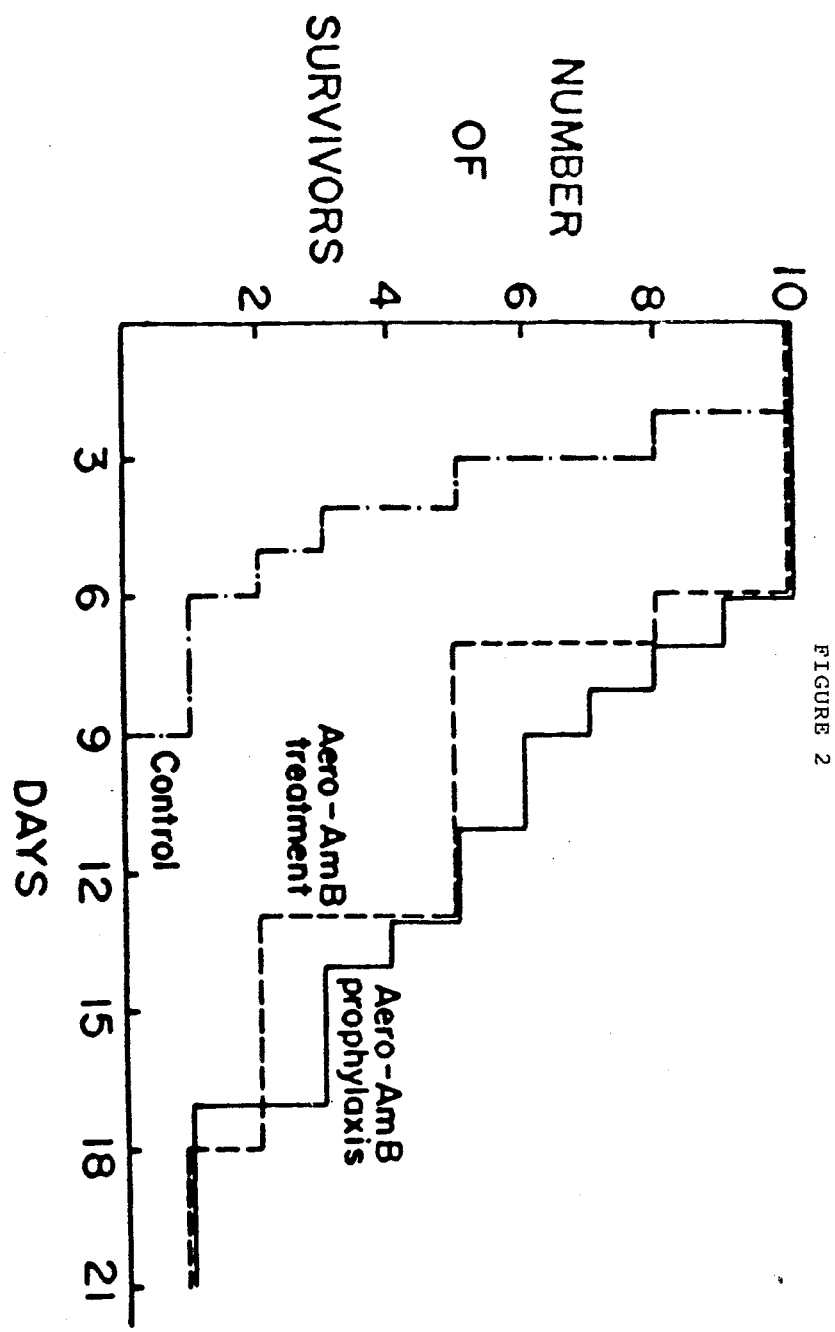
FIG. 2 shows the survival of animals in trial 2. Control animals received no therapy; animals in the aero-AmB prophylaxis group received 1.6 mg/kg aerosolized amphotericin B two days prior to infection; animals in the aero-AmB treatment group received daily aerosolized amphotericin B, for 6 consecutive days, first dose given 24 hours after infection.

Trial 2. Animals in groups of ten received either no medication, a single dose of 1.6 mg/kg aero-AmB two days prior to infection, or 1.6 mg/kg aero-AmB given 24 hours after infection and then daily for six days (treatment group). Survival was monitored daily. Whereas all control animals had died by day nine, prophylactically administered aero-AmB delayed death, with 50% of animals still alive on day 13. The same dose of aero-AmB given as treatment was similarly effective in delaying mortality (FIG. 2).

Pulmonary Deposition and Activity of Aerosol Amphotericin B

Trial 3. Animals in groups of six received no medication (control group) or three different doses of aero-AmB once, two days prior to infection. Group 1 was given 4.5 ml of a 5 mg/ml amphotericin B solution (1.6 mg/kg); group 2, 4.5 ml of a 10 mg/ml solution (3.2 mg/kg); group 3, 9.0 ml of a 10 mg/ml (6.4 mg/kg).

All animals were sacrificed 24 hours after infection. Their lungs were removed, weighed, diluted 1:10 with normal sterile saline and grounded in a tissue grinder. This was then diluted in saline to yield a 1:10000 dilution. One-ml portions of these were poured into Petri dishes and mixed with 10 ml SDA. Plates were incubated at 35° C. and read after 48 hours. There was about a sixfold reduction in the number of CFUs recovered from the lungs of infected animals that had received 1.6 mg/kg aero-AmB compared to the control group, and again a sixfold reduction with a doubling of the dose (table 1). The reduction in CFUs per gram of lung was dose related, reaching a maximum of eightyfold versus controls with 6.4 mg/kg.

Trial 4. As in trial 3, animals in groups of 6 received aero-AmB in doses of either 1.6, 3.2 or 6.4 mg/kg and were sacrificed after 48 hours. Lungs, liver, kidney, and spleen were removed, weighed, diluted 1:5 with sterile normal saline and homogenized in a tissue grinder. In addition, a blood sample was obtained via cardiac puncture prior to death. Amphotericin B levels were determined by bioassay (7). The sensitivity of the test was 0.05 mcg/g for fluids and 8 mcg/g for tissues. The correlation coefficient for the standard curve of the bioassay was 0.977. Two days after receiving aero-AmB, amphotericin B could not be detected in liver, kidney, spleen or serum from any animal. Amphotericin B was only detected in lungs of animals receiving 3.2 or 6.4 mg/kg aero-AmB (table 2).

Experimental Discussion

Aero-AmB given as prophylaxis or as therapy in a rat model of pulmonary aspergillosis reduced or delayed mortality. Two days after single doses of 3.2 or 6.4 mg/kg or aero-AmB, remarkably high concentrations of amphotericin B were achieved in the lungs—levels that with intravenous administration in humans can only be achieved after weeks of treatment. Based on preliminary pharmacokinetic studies, concentrations in the lung of about 7 mcg/g can be achieved with a single dose of 0.8 mg/kg aero-AmB. This concentration exceeds by nearly tenfold the minimum fungicidal concentrations of amphotericin B for most strains of *A. fumigatus*.

No amphotericin B could be detected in liver, kidney or spleen—organs in which the highest drug concentrations are recovered after intravenous administration (7). Unfortunately, the bioassay is not sensitive enough to detect concentrations of amphotericin B below 8 mcg/g tissue.

Outbreaks of aspergillosis have been reported from several hospitals where patients were exposed to increased levels of aspergillus spores in the air because of nearby construction or renovation (14, 15). Conversely, a decrease in the number of aspergillus spores in air by means of filters was associated with a decrease in the number of patients developing pulmonary aspergillosis (10, 11).

Similarly, in our animal model mortality over time increased when higher inocula of aspergillus spores were injected intratracheally, and decreased with lower inocula (data not shown). Thus, the reduction in the number of viable spores in animals receiving aero-AmB is likely to be a major factor improving survival. The data from trial 1, 2 and 3 indicate, that amphotericin B delivered as an aerosol was biologically available and active.

In addition to killing spores, aero-AmB deposited in the lungs can act by inhibiting mycelial proliferation:

the fact that aero-AmB was active when given as therapy 24 hours after infection strongly supports this view.

Amphotericin B has been used previously as local therapy for fungal infections: in one study 50 mg given orally decreased proven episodes of invasive candidiasis (16). Other fungal infections that have been treated with local therapy include rhino-orbital mucormycosis (17), necrotizing scleritis due to *A. oryzae* (18), urinary tract infections with Candida sp., (19, 20), meningitis (21), and cavitary lung lesions (aspergillomas) (22, 23, 24, 25).

In these latter reports, many patients responded favorably. Single doses of up to 50 mg in 10–20 ml of 5% dextrose in water and total doses of 500 mg were well tolerated; only one patient had dose-limiting toxicity (22). No signs of systemic absorption or toxicity were noted. In two patients no amphotericin B could be detected in blood after endobronchial installation of 5 mg amphotericin B (24).

In a recent prospective, randomized trial, amphotericin B as a nasal spray (10 mg/day in 3 divided doses) was given to patients with neutropenia and fever (26). 1/28 patients receiving local amphotericin B developed invasive aspergillosis as compared to 5/30 patients in the control group. It has been calculated, that with 3 CFU of *A. fumigatus* spores per $m^3$ air the "average adult" with a respiratory rate of 20 and a tidal volume of 500 ml inhales about 40 spores a day, 20 of which are deposited in the upper respiratory tract and 7 reaching the alveoli (24). Thus, it is quite probable that a large number of Aspergillus spores are inhaled everyday directly into the distant airways without ever going through the nose or sinuses. Unlike the subject use of aerosol amphotericin B, nasal amphotericin B is unlikely to reach such distant airways sufficiently and therefore cannot prevent invasive aspergillosis that results from deposition of spores in the lung periphery. Additionally, the nasal inhalation is effected by an atomizer which produces a majority of particles larger than 10 μm which is also not sufficient to reach distant airways in the lungs. In one study eight of eighteen patients with invasive aspergillosis had sterile nasal cultures (27).

Treatment of pulmonary fungal infections with aerosolized nystatin was first reported in 1956 (28) and 1958 (29, 30). Kilburn administered aerosolized amphotericin B in six dogs and described it as "innocuous treatment" (31). She subsequently treated one patient with "endobronchial histoplasmosis" for 60 days with 1 mg/kg amphotericin B/day. Initially, the patient developed cough and increased sputum production, but thereafter "there was no discomfort". No details about the nebulizer used were given and treatment results were reported as "equivocal". Therefore, there was no showing that aerosolized amphotericin B was effective in treatment of endobronchial histoplasmosis nor was there any teaching of the use of aerosol amphotericin B in prevention of infection. Additionally, there are no effective dose ranges nor particle sizes given.

TABLE 1

Number of CFUs of aspergilli recovered from 1:10000 dilutions of lung homogenates 24 hours after infection and 72 hours after a single dose of aero-AmB.

| | | Doses of aero-AmB | | |
|---|---|---|---|---|
| | Control | 1.6 mg/kg | 3.2 mg/kg | 6.4 mg/kg |
| MEDIAN: | 56.5 | 8.7 | 1.4 | 0.7 |
| SD: | 18.2 | 9.4 | 1.6 | 1.1 |
| RANGE: | 25–82 | 0–29 | 0–4 | 0–3 |

TABLE 2

Mean Tissue Concentration of Amphotericin B at 48 Hours after a Single Dose of Aero-AmB.

| | Doses of aero-AmB | | |
|---|---|---|---|
| | 1.6 mg/kg | 3.2 mg/kg | 6.4 mg/kg |
| LUNGS | nma* | 13.9 ± 0.7** | 27.4 ± 5.1 |
| LIVER | nma* | nma* | nma* |
| KIDNEY | nma* | nma* | nma* |
| SPLEEN | nma* | nma* | nma* |
| SERUM | nma* | nma* | nma* |

*No measurable amount (<8 mcg/g)
**Mean ± SD; mcg/g; n = 6

REFERENCES

1. Cordonnier, C., Beranaudin, J. F., Bierling, P., Huet, Y., Vernant, J. P. Pulmonary complications occurring after allogeneic bone marrow transplantation. Cancer 1986; 58: 1047–54.
2. Swerdlow, B., Deresinsky, S. Development of aspergillus sinusitis in a patient receiving amphotericin B. Am J Med 1984; 76: 162–6.
3. Viollier, A. F., Peterson, D. E., DeJongh, C. A., Newman, K. A., Gray, W. C., Sutherland, J. C., Moody, M. A., Schimpff, S. C. Aspergillus sinusitis in cancer patients. Cancer 1986; 58: 366–71.
4. Schubert, M. M., Peterson, D. E., Meyers, J. D., Hackman, R., Thomas, E.D. Head and neck aspergillosis in patients undergoing bone marrow transplantation. Cancer 1986; 57: 1092–6.
5. Barson, W. J, Ruymann, F. B. Palmar aspergillosis in immunocomprimised children. Ped Infect Dis 1986; 5: 264–8
6. Allo, M. D., Miller, J., Townsend, T., Tan, C., Primary cutaneous aspergillosis associated with Hickman intravenous caters. N Engl J Med 1987; 317: 1105–8
7. Christiansen, K. J., Bernard, E. M., Gold, J. W. M., Armstrong, D. Distribution and activity of amphotericin B in humans. J Infect Dis 1985; 152: 1037–43
8. Rosen, P. P., Sternberg, S. S. Decreased frequency of aspergillosis and mucormycosis. N Engl J Med 1976; 23: 1319–20
9. Rose, H. D., Mechanical control of hospital ventilation ad aspergillus infections. Am Rev Resp Dis 1972; 105: 306–7
10. Sherertz, R. J., Belani, A., Kramer, B. S., Elfenbein, G. J., Weiner, R. S., Sullivan, M. L, Thomas, R. G. Impact of air filtration on nosocomial aspergillus infections. Unique risk of bone marrow transplant recipients. Am J Med 1987; 83: 709–18
11. Rhame, F. S., Streifel, A. J., Kersey, J. H., McGlave, P. B. Extrinsic risk factors for pneumonia in the patient at high risk of infection. Am J Med 1984; 76 (suppl 5A): 42–52
12. Schmitt, H. J., Bernard, E. M., Andrade, J., Edwards, F., Schmitt, B., Armstrong, D. MIC and fungicidal activity of terbinafine against clinical isolates of Aspergillus spp. Antimicrob Agents Chemother 1988; in press
13. Schmitt, H. J., Bernard, E. M., Andrade, J., Edwards, F., Armstrong, D. An improved animal model for pulmonary aspergillosis. Program and abstracts of the 27th Interscience Conference on Antimicrobial Agents and Chemotherapy, New York, Oct. 4–7, 1987; Abstract number 780)
14. Arnow, P. M., Anderson, R. L., Mainous, P. D., Smith, E. J. Pulmonary aspergillosis during hospital renovation. Am Rev Resp Dis 1978; 118: 49–53
15. Lentino, J. R., Rosenkranz, M. A., Michaels, J. A., Kurup, V. P., Rose, H. D., Rytel, M. W. A retrospective review of airborne disease secondary to road construction and contaminated air conditioners. Am J Epidemiol 1982; 116: 430–7
16. Ezdinli, E. Z., O'Sullivan, D. D., Wasser, L. P., Kim, U., Stutzman, L. Oral amphotericin B for candidiasis in patients with hematologic neoplasms. JAMA 1979; 242: 258–60
17. Kohn, R., Hepler, R. Management of limited rhino-orbital mucormycosis without exteration. Ophthalmology 1985; 92: 1440–4
18. Stenson, S., Brookner, A., Roenthal, S. Bilateral endogenous necrotizing scleritis due to aspergillus oryzae. Ann Ophthalmol 1982; 14: 67–72
19. Walzer, Y., Bear, R. A. Ureteral obstruction of renal transplant due to ureteral condidiasis. Urology 1983; 3: 295–7
20. Domart, Y., Delmas, V., Cornud, F., Bouchma, A., Chastre, J., Gilbert, C. Obstruction des voies urinaires par des bezoars candidosiques ou "fungus balls". Press Medicale 1986; 15: 153–6
21. Polsky, B., Depman, M. R., Gold J. W. M., Galicich, J. H., Armstrong, D. Intraventricular therapy of cryptococcal meningitis via a subcutaneous reservoir. Am J Med 1986; 81: 24–8
22. Hargis, P. L., Bone, K. C., Stewart, P., Rector., N., Hiller, C. Intracavitary amphotericin B in the treatment of symptomatic pulmonary aspergillomas. Am J Med 1980; 68: 389–94
23. Adelson, H. T., Malcolm, J. A. Endocavitary treatment of pulmonary mycetomas. Am Rev Resp Dis 1968; 98: 87–92
24. Ramirez-R. J., Pulmonary aspergilloma. Endobronchial treatment. N Engl J Med 1964; 271: 1281–5
25. Krakowka, P., Traczyk, K., Walczak, J., Halweg, H., Elsner, Z., Pawlicka, L. Local treatment of aspergilloma of the lung with a paste containing nystatin or amphotericin B. Tubercle 1970; 51: 184–191
26. Meunier, F., Leleux, A., Gerain, J., Ninove, D., Snoeck, R., Klastersky, J. Prophylaxis of aspergillosis in neutropenic cancer patients with nasal spray of amphotericin B: a prospective randomized study. Program and abstracts of the 27th Interscience Conference on Antimicrobial Agents and Chemotherapy, New York, Oct. 4–7, 1987; Abstract number 1346
27. Aisner, J., Murillo, J., Schimpff, S. C., Steere A. C. Invasive aspergillosis in acute leukemia: correlation with nose cultures and antibiotic use. Ann Intern Med 1979; 90: 4–9
28. Riddell, R. W. Fungous Diseases of Britain. Br Med J 1959; 2: 783–92
29. Gero, S., Szekely, J. Pulmonary moniliasis treated with nystatin aerosol. Lancet 1958; 2: 1229–30
30. McKendrick, D. W., Medlock, J. M. Pulmonary moniliasis treated with nystatin aerosol. Lancet 1958; 1: 621–2
31. Kilburn, K. H. The innocuousness and possible therapeutic use of aerosol amphotericin B. Am Rev Resp Dis 1959; 80: 441–2
32. Vieira, D. F., Van Saene, H. K., Miranda, D. R. Invasive pulmonary aspergillosis after near-drowning. Intensive Care Med 1984; 10: 203–4
33. Ikemoto, H., Watanabe, K., Mori, T. Pulmonary Aspergilloma; 30–5
34. Rodenhuis, S., Beaumont, F., Kauffman, H. F., Sluiter, H. J. Invasive pulmonary aspergillosis in a non-immunosuppressed patient: successful management with sysemic amphotericin and flucytosine and inhaled amphotericin. Thorax 1984; 39: 78–9

What is claimed is:

1. A method of preventing a pulmonary infection by Asperigillus in a subject susceptible to infection by Aspergillus comprising administering to the subject from about 0.01 mg/kg to about 6.0 mg/kg of a polyene or a pharmaceutically acceptable derivative thereof in an aerosol of particles having an aerodynamic diameter between about 0.5 um and about 8.0 um thereof, effective to prevent pulmonary infection by Aspergillus.

2. The method of claim 1, wherein the polyene is amphotericin B.

3. The method of claim 1, wherein the polyene is pimaricin.

4. The method of claim 1, wherein the subject is a human.

5. The method of claim 4, wherein the human is immunosuppresed.

6. The method of claim 1, wherein the infection is pulmonary aspergillosis.

7. The method of claim 6, wherein the infection is caused by Aspergillus fumigatus.

8. The method of claim 1, wherein the polyene or a pharmaceutically acceptable derivative thereof is administered by intranasal inhalation.

9. The method of claim 1, wherein the polyene or a pharmaceutically acceptable derivative thereof is administered by oral inhalation.

10. The method of claim 1, wherein the polyene or a pharmaceutically acceptable derivative thereof is administered as particles additionally having a mass median aerodynamic diameter between about 1 $\mu$m and about 6 $\mu$m.

11. The method of claim 1, wherein the particles are produced by an ultrasonic nebulizer.

12. The method of claim 1, wherein the amount per dose of the polyene administered to the subject is between about 0.4 mg/kg and about 5.0 mg/kg.

13. The method of claim 1, wherein the amount per dose of the polyene administered to the subject is between about 0.8 mg/kg and about 4.0 mg/kg.

14. The method of claim 13, wherein the amount per dose of the polyene administered to the subject is between about 1.6 mg/kg and 3.2 mg/kg.

15. The method of claim 1, wherein the polyene is administered 3 to 14 times in 1 to 6 weeks and thereafter weekly or twice a week.

16. The method of claim 15, wherein the polyene is administered daily for 1 week and thereafter is administered twice a week.

17. A method of treating pulmonary aspergillosis in a subject comprising administering to the subject from about 0.01 mg/kg to about 8.0 mg/kg of a polyene or a pharmaceutically acceptable derivative thereof in an aerosol of particles having an aerodynamic diameter between about 0.5 um and about 8.0 um effective to treat aspergillosis.

18. The method of claim 17, wherein the polyene is amphotericin B.

19. The method of claim 17, wherein the polyene is pimaricin.

20. The method of claim 17, wherein the subject is a human.

21. The method of claim 17, wherein the Aspergillosis is caused by *Aspergillus fumigatus*.

22. The method of claim 21, wherein the polyene is administered by intranasal inhalation.

23. The method of claim 21, wherein the polyene is administered by oral inhalation.

24. The method of claim 17, wherein the polyene or a pharmaceutically acceptable derivative thereof is administered as particles additionally having a mass median aerodynamic diameter between about 1 μm and about 6 μm.

25. The method of claim 17, wherein the particles are produced by an ultrasonic nebulizer.

26. The method of claim 17, wherein the amount per dose of the polyene or a pharmaceutically acceptable derivative thereof administered to the subject is between about 0.2 mg/kg and about 6.0 mg/kg.

27. The method of claim 17, wherein the amount per dose of the polyene or a pharmaceutically acceptable derivative thereof administered to the subject is between about 0.8 mg/kg and about 5.0 mg/kg.

28. The method of claim 27, wherein the amount per dose of the polyene or a pharmaceutically acceptable derivative thereof administered to the subject is between about 1.6 mg/kg and about 4.0 mg/kg.

29. The method of claim 17, wherein the polyene is administered 1 to 8 times daily.

30. The method of claim 29, wherein the polyene is administered 2 times day.

31. The method of claim 29, wherein the polyene is administered for 7 to 28 days.

32. A composition for the prevention or treatment of infection by a aspergillus, comprising an amount of a polyene or a pharmaceutically acceptable derivative thereof in an aerosol spray which comprises particles having an aerodynamic diameter between about 0.5 μm and about 8.0 μm, the composition being effective to prevent or treat pulmonary infection by a aspergillus and thus prevent or treat the infection, and a pharmaceutically acceptable carrier.

33. The composition of claim 32, wherein the polyene is amphotericin B.

34. The composition of claim 32, wherein the polyene is pimaricin.

35. The composition of claim 32, wherein the particles additionally have a mass median aerodynamic diameter between about 1 μm and about 6 μm.

36. A composition useful for aerosol administration for the prevention or treatment of infection by a aspergillus comprising between about 1 mg and about 300 mg of a polyene or a pharmaceutically acceptable derivative thereof per ml. of pharmaceutical acceptable carrier, wherein he aerosol particles have an aerodynamic diameter between about 0.5 um and about 8.0 um.

37. The composition of claim 36, wherein at least 55% of the particles have an aerodynamic diameter between about 0.5 μm and about 8.0 μm.

38. The composition of claim 36, wherein the amount of the polyene or the pharmaceutically acceptable derivative thereof is between about 10 mg and about 200 mg.

39. The composition of claim 38, wherein the amount of the polyene or the pharmaceutically acceptable derivative thereof is between about 30 mg and about 120 mg.

40. A composition useful for aerosol administration for the prevention or treatment of infection by a aspergillus comprising between about 1 mg and about 100 mg of a polyene or a pharmaceutically acceptable derivative thereof, per ml of a pharmaceutically acceptable carrier wherein the aerosol particles have been aerodynamic diameter between about 0.5 um and about 8.0 um.

41. The composition of claim 40, wherein the polyene is amphotericin B.

42. The composition of claim 40, wherein the polyene is pimaricin.

43. The composition of claim 40, wherein the amount of the polyene or a pharmaceutically acceptable derivative thereof is between about 10 mg and about 60 mg.

* * * * *